(12) United States Patent
Lee et al.

(10) Patent No.: US 7,063,680 B2
(45) Date of Patent: *Jun. 20, 2006

(54) SURGICAL APPARATUS

(75) Inventors: Eric Lee, Irvine, CA (US); Grace C. Liao, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/232,176

(22) Filed: Sep. 21, 2005

(65) Prior Publication Data

US 2006/0052740 A1    Mar. 9, 2006

Related U.S. Application Data

(63) Continuation-in-part of application No. 11/011,417, filed on Dec. 14, 2004, which is a continuation-in-part of application No. 10/937,065, filed on Sep. 9, 2004.

(51) Int. Cl.
*A61B 17/20* (2006.01)

(52) U.S. Cl. .............. 604/22; 604/22; 604/533; 604/43

(58) Field of Classification Search .......... 604/27, 604/275, 334, 107, 108, 550, 22, 500, 264, 604/35, 39, 43, 521, 44, 533; 606/107, 108, 606/169, 4.41, 6; 623/6.12, 6.56; 73/865.9
See application file for complete search history.

(56) References Cited

U.S. PATENT DOCUMENTS

| | | | | |
|---|---|---|---|---|
| 4,386,927 A | * | 6/1983 | Eichenbaum | 604/541 |
| 5,151,084 A | * | 9/1992 | Khek | 604/22 |
| 5,830,192 A | * | 11/1998 | Van Voorhis | 604/533 |
| 6,013,049 A | * | 1/2000 | Rockley et al. | 604/22 |
| 6,340,355 B1 | * | 1/2002 | Barrett | 604/27 |
| 6,579,270 B1 | | 6/2003 | Sussman et al. | |
| 6,852,093 B1 | | 2/2005 | Boukhny | |
| 2003/0004455 A1 | * | 1/2003 | Kadziauskas et al. | 604/27 |
| 2003/0069594 A1 | * | 4/2003 | Rockley et al. | 606/169 |
| 2003/0208218 A1 | | 11/2003 | Kadziauskas | |
| 2004/0068270 A1 | | 4/2004 | Allred | |
| 2004/0089080 A1 | | 5/2004 | Kadziauskas | |
| 2004/0153093 A1 | | 8/2004 | Donovan | |

* cited by examiner

*Primary Examiner*—Nicholas D. Lucchesi
*Assistant Examiner*—Aamer S. Ahmed
(74) *Attorney, Agent, or Firm*—Jeffrey S. Schira

(57) ABSTRACT

A method of conducting traditional two-handed phacoemulsification through two relatively small incisions by using a phacoemulsification tip/sleeve along with a second irrigation tip, with or without an attached manipulation tool.

7 Claims, 3 Drawing Sheets

SURGICAL APPARATUS

This application is a continuation-in-part of U.S. patent application Ser. No. 11/011,417, filed Dec. 14, 2004, currently co-pending, which is a continuation-in-part of U.S. patent application Ser. No. 10/937,065, filed Sep. 9, 2004, also currently co-pending.

BACKGROUND OF THE INVENTION

This invention relates generally to the field of cataract surgery and more particularly to a method and apparatus for bi-manual phacoemulsification surgery.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light that can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical handpiece suitable for phacoemulsification procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

A modified phacoemulsification technique called "bimanual" phacoemulsification has been adopted by many surgeons. With the bimanual technique, the irrigation sleeve is removed from around the ultrasonically drive tip. This allows for the small tip to be inserted into the eye through a smaller incision. Irrigation fluid is supplied by a second irrigating tip. Additional information concerning traditional phacoemulsification and bimanual phacoemulsification is included in U.S. Patent Publication No. US 2003/0004455 A1. And in particular, Paragraphs [0001] through [0008], which are incorporated herein by reference. As described in this reference, traditional phacoemulsification tips/irrigation sleeves have a larger overall diameter, requiring a larger incision. Traditional phacoemulsification tips/irrigation sleeves are also described as causing "roiling" in the area immediately in front of the phaco tip, and visibility-reducing "clouding" of debris. According to this reference, a bimanual technique solves these and other problems. In the bimanual technique, the incision may be smaller because the irrigation sleeve on the ultrasonic tip is not used, but without the sleeve, there is direct contact between the vibrating tip and the tissue at the wound. This can result in extra stress on the wound tissue, delaying healing and possibly requiring the use of a suture to seal the wound at the completion of surgery. The soft irrigation sleeve also acts to seal the wound from leakage during surgery. Without the use of the irrigation sleeve, excessive wound leakage can cause shallowing of the anterior chamber, excessive turbulence and premature removal of the protective viscoelastic material. Excessive wound leakage can also cause over-hydration of the wound tissue, possibly resulting in edema.

Therefore, a need continues to exist for a method and device for conducting phacoemulsification through a small incision.

BRIEF SUMMARY OF THE INVENTION

The inventors of the present invention have discovered that traditional one-handed phacoemulsification can be conducted through a relatively small incision by reducing the diameter of the phacoemulsification tip/sleeve. A second irrigation tip, with or without an attached manipulation tool, may also be used to provide addition irrigation. Such an arrangement minimizes wound leakage, thereby helping to avoid over-hydration of the wound, low intraocular pressure, excessive turbulence and premature removal of the viscoelastic material.

Accordingly, one objective of the present invention is to provide a method for two-handed phacoemulsification with irrigation directed through both incisions.

Another objective of the present invention is to provide a small incision phacoemulsification method and apparatus having reduced wound leakage.

Another objective of the present invention is to provide a small incision phacoemulsification method and apparatus having reduced turbulence.

Another objective of the present invention is to provide a small incision phacoemulsification method and apparatus that minimized premature removal of the viscoelastic material.

Another objective of the present invention is to provide a small incision phacoemulsification method and apparatus that minimizes wound hydration.

These and other advantages and objectives of the present invention will become apparent from the detailed description and claims that follow.

DETAILED DESCRIPTION OF THE INVENTION

Figure 1:
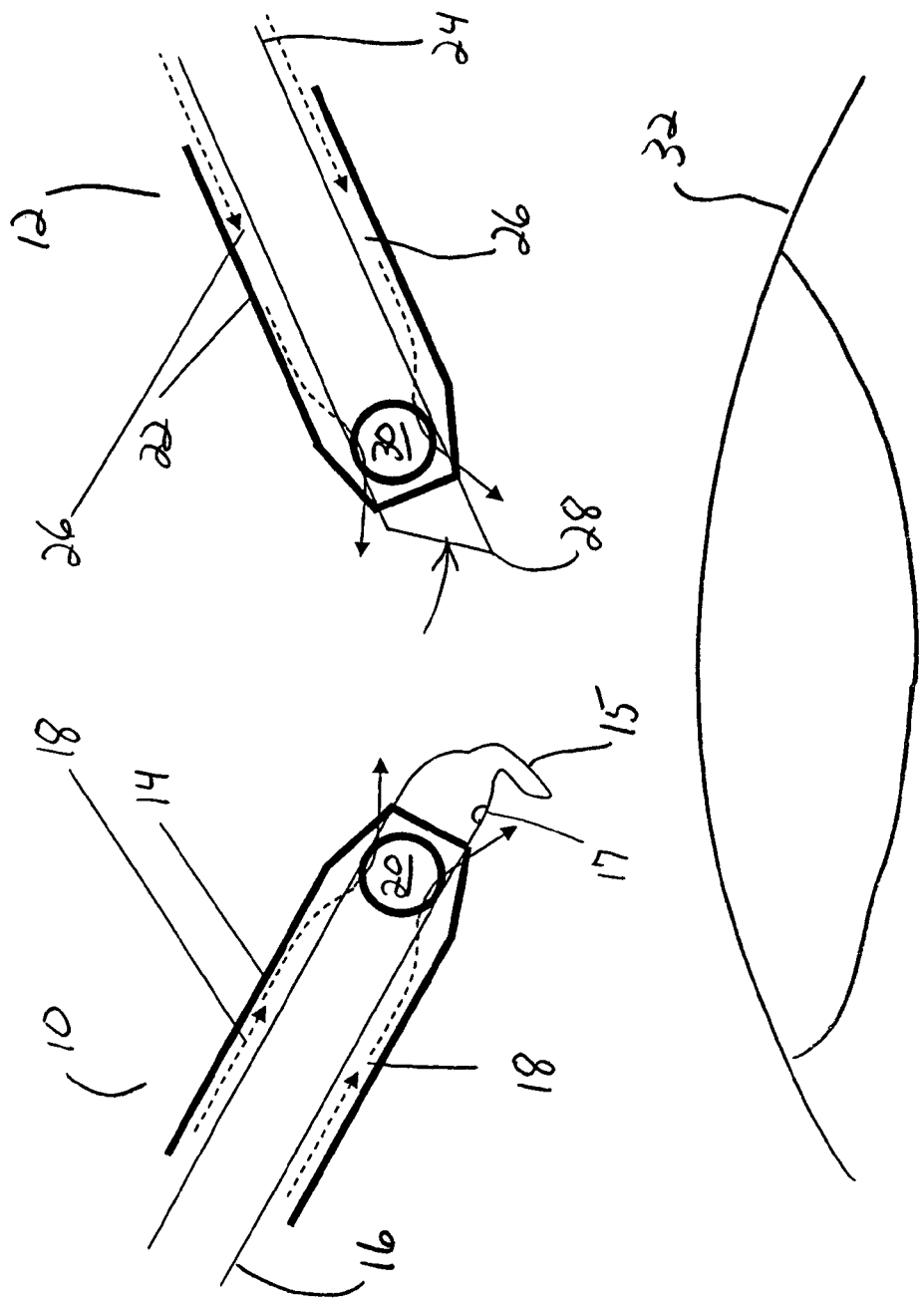
FIG. 1 is a partial cross-section of the phacoemulsification and irrigation/aspiration tips that may be used with the present invention.
Figure 3:
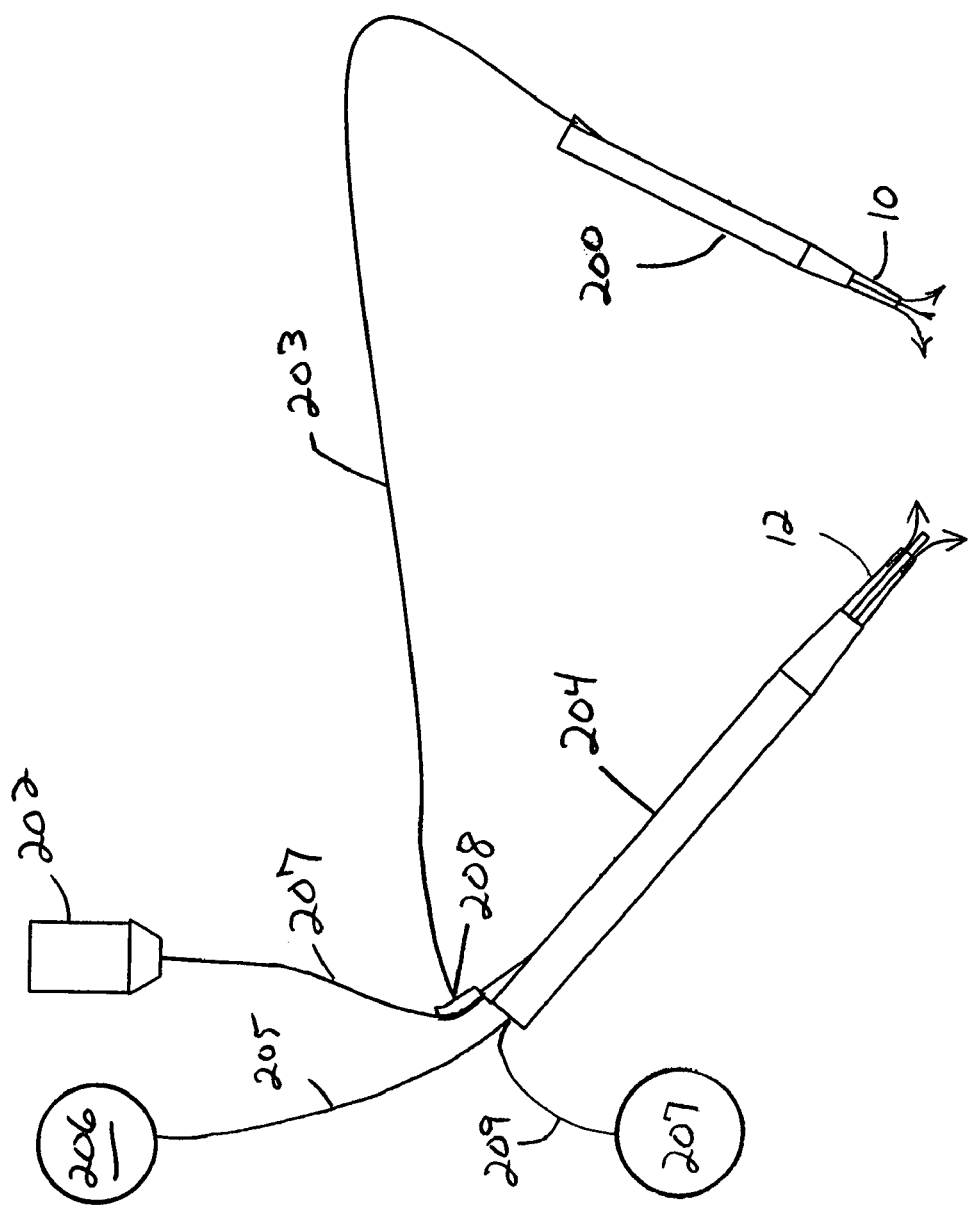
FIG. 3 is a schematic illustration of a phacoemulsification handpiece and irrigation handpiece being used for the bi-manual phacoemulsification surgical procedure of the present invention.

As seen in FIGS. 1 and 3, the method of the present invention is generally practiced using irrigation tip 10 and phacoemulsification tip 12 simultaneously in what is called a "Bi-Manual" surgical technique. Irrigation tip 10 may be any conventional irrigation tip and may include irrigation port 17 and flexible outer silicone sleeve 14 and inner tube 16. Inner tube 16 may also be formed with hook 15 or some other manipulation device. Space 18 between sleeve 14 and tube 16 defines a pathway for irrigating solution to flow out port 20 and into the surgical site. Port 17 can be used as an additional irrigation port, and irrigating solution may be expressed out of ports 17 and 20. Phacoemulsification tip 12 is of similar construction and generally contains flexible outer silicone sleeve 22 and inner tube 24 defining a first irrigating fluid path 26 that allows irrigating fluid to flow out of port 30. Inner tube 24 contains open distal end 28 allowing material to be aspirated through inner tube 24. Preferably, phacoemulsification tip 12 has a reduced overall diameter, on the order of 0.8 mm to 1.0 mm. Such a small diameter permits an incision size of preferably less than around 2.4 mm in width, even more preferably less than around 2.2 mm in width, and even more preferably less than around 2.0 mm in width, and even more preferably less than around 1.8 mm in width and most preferably less than around 1.6 mm in width. Alternatively, tip may be a liquefracturing tip similar to the AQUALASE® tip sold by Alcon Laboratories, Inc., Fort Worth, Tex. and described more fully in U.S. Pat. No. 6,579,270 B2 (Sussman, et al.) at FIGS. 23 and 24 and column 7, lines 32–45, the contents of which being incorporated herein by reference.

Figure 2:
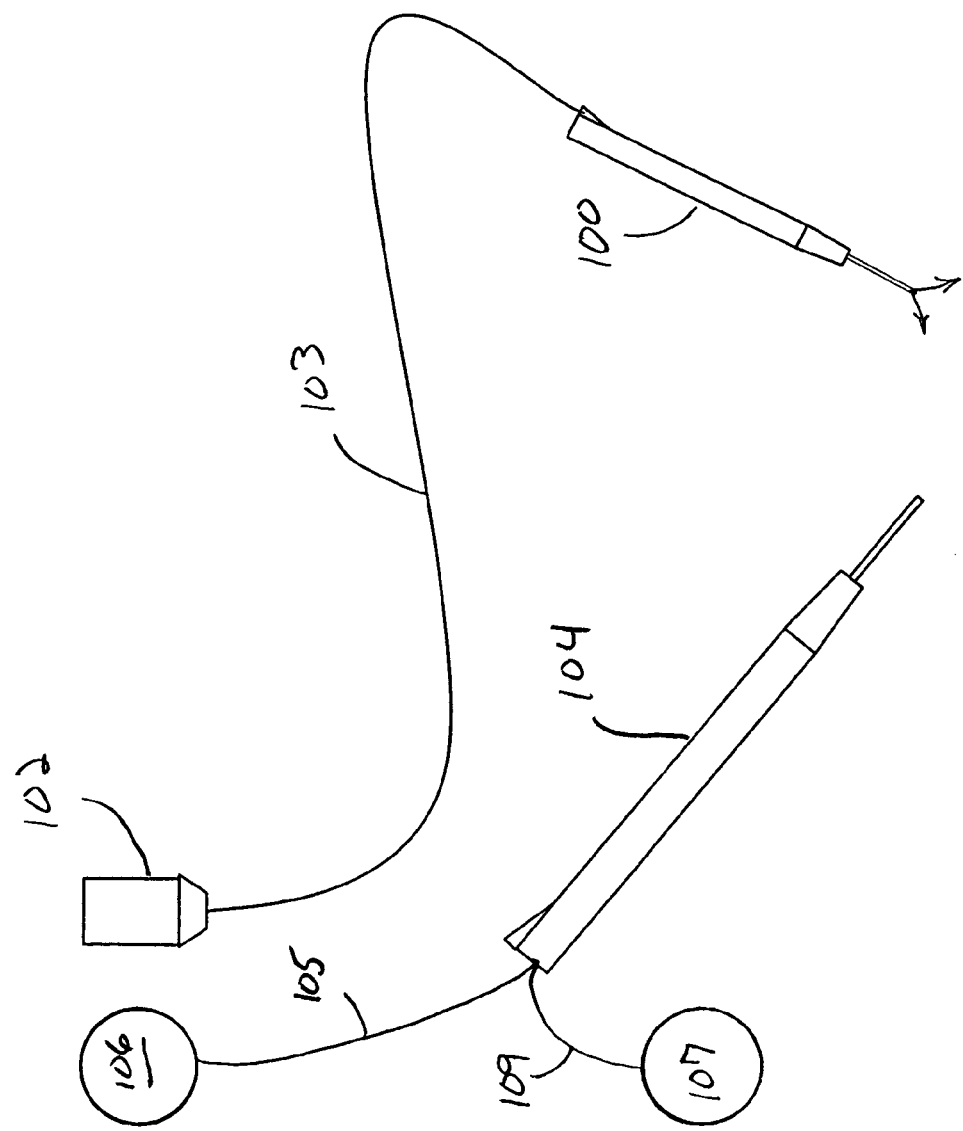
FIG. 2 is a schematic illustration of a phacoemulsification handpiece and irrigation/aspiration handpiece being used for a traditional bi-manual phacoemulsification surgical procedure.

As best seen in FIG. 2, in a traditional bimanual phacoemulsification technique, irrigation/aspiration handpiece 100 is connected to pressurized or elevated source of irrigation fluid 102 through tubing 103. Ultrasound handpiece 104 is connected to aspiration pump 106 through tubing 105 and to ultrasound driver 107 through cable 109. Ultrasound handpiece 104 is not connected to source 102 and does not have any irrigation capabilities.

As seen in FIGS. 1 and 3, in use, irrigation handpiece 200, having tip 10, is connected to pressurized or elevated source of irrigation fluid 202 through tubing 207, fitting 208 and tubing 203. Ultrasound handpiece 204, having tip 12, is connected to aspiration pump 206 through tubing 205, to source 202 through tubing 207 and fitting 208 and to ultrasound driver 207 through cable 209. Preferably, fitting 208 is located at handpiece 204. Accordingly, both handpiece 200 and handpiece 204 have a common irrigation source and both provide an irrigation function. Irrigation tip 10 is held in one hand by the surgeon and used in a conventional manner to provide an irrigating fluid, such as a saline solution, into eye 32 to help maintain the integrity of the eye and prevent anterior chamber collapse. Phacoemulsification tip 12 is held in the other hand by the surgeon and is connected to a suitable ultrasound handpiece. One suitable handpiece is the INFINITI® system handpiece available commercially from by Alcon Laboratories, Inc., Worth, Tex. Phacoemulsification tip 12 is used to conduct a traditional phacoemulsification technique during which an irrigating fluid, such as a saline solution, is introduced into eye 32 through fluid path 26 and port 30 and debris is aspirated from eye 32 through distal end 28 and inner tube 24. Such an arrangement prevents direct contact between vibrating inner tube 24.

This description is given for purposes of illustration and explanation. It will be apparent to those skilled in the relevant art that changes and modifications may be made to the invention described above without departing from its scope or spirit.

We claim:
1. A surgical apparatus, comprising:
   a) a first irrigation handpiece having an irrigation tip, the irrigation tip having a first inner tube covered by a first outer flexible sleeve, a space between the first inner tube and the first outer sleeve creating a first irrigation fluid path;
   b) a second handpiece having a tip, the tip having a hollow second inner tube covered by a second outer flexible sleeve, a space between the second inner tube and the second outer sleeve creating a second irrigation fluid path the second outer sleeve being sized so at to permit the tip of the second handpiece to pass through an incision of less than 2.4 mm in width;
   c) the first irrigation handpiece and the second handpiece being connected by a fitting at the second handpiece to at least one source of irrigation fluid so as to provide irrigating fluid to the surgical site through both the first irrigation path and the second irrigation path;
   d) an ultrasound driver connected to the second handpiece so as to vibrate the second inner tube; and
   e) as aspiration pump connected to the second tube so as to aspirate material from the surgical site through the second hollow inner tube.

2. The apparatus of claim 1 wherein the irrigating fluid is provided to the surgical site through both the first irrigation path and the second irrigation path from a common source of irrigation fluid.

3. The apparatus of claim 1 wherein the incision is less than around 2.2 mm in width.

4. The apparatus of claim 1 wherein the incision is less than around 2.0 mm in width.

5. The apparatus of claim 1 wherein the incision is less than around 1.8 mm in width.

6. The apparatus of claim 1 wherein the incision is less than around 1.6 mm in width.

7. The apparatus of claim 1 wherein the incision is between around 1.6 mm and 2.4 mm in width.

* * * * *